United States Patent [19]

Cropley

[11] 4,125,553

[45] Nov. 14, 1978

[54] PROCESS FOR MAKING OXYGENATED CARBON COMPOUNDS

[75] Inventor: Jean B. Cropley, South Charleston, W. Va.

[73] Assignee: Union Carbide Corporation, New York, N.Y.

[21] Appl. No.: 748,766

[22] Filed: Dec. 8, 1976

Related U.S. Application Data

[63] Continuation of Ser. No. 590,718, Jun. 26, 1975, abandoned.

[51] Int. Cl.$^2$ ............................................. C07C 27/06
[52] U.S. Cl. ........................... 260/449 R; 260/449 M
[58] Field of Search ................................. 260/449 R

[56] References Cited

U.S. PATENT DOCUMENTS

| Re. 19,243 | 7/1934 | Richardson | 260/449 R X |
|---|---|---|---|
| 1,984,884 | 12/1934 | Lazier | 260/449 R |
| 2,503,291 | 4/1950 | Odell | 260/449 R |
| 2,506,221 | 5/1950 | Keith | 260/449 R |
| 2,662,911 | 12/1953 | Dorschner et al. | 260/449 |
| 2,740,803 | 4/1956 | Dorschner | 260/449 R |

OTHER PUBLICATIONS

Fischer et al., Brenn Chemie 17, 265-285 (1925).
Fischer et al., Brenn Chemie 16, 466-469 (1935).
Pichler, Brenn Chemie 19, 226t (1939) Translation.
Kratel, Doctoral Dissertation, Tech Hochschule zu Berlin-Charlottenburg, 1937.
Eidus et al., Transfrom Izves, Akad. Nank, SSSR Ser Khim, 7, 1160-1169, Jul. 1965.
Schultz et al., Bureau Mines Report No. 6974.
Hougen et al., Chemical Process Principles, Kinetics & Catalysis, Part 3, J. Wiley, New York, 1947, 1031-1033.

*Primary Examiner*—Howard T. Mars
*Attorney, Agent, or Firm*—Bernard Lieberman

[57] ABSTRACT

The invention involves controlling reaction conditions of a highly exothermic reaction to produce oxygenated two carbon atom compounds such as acetic acid, acetaldehyde and ethanol.

1 Claim, No Drawings

PROCESS FOR MAKING OXYGENATED CARBON COMPOUNDS

This application is a continuation of our prior U.S. application Ser. No. 590,718, filed June 26, 1975, abandoned.

This invention is concerned with the continuous production of oxygenated carbon compounds which predominantly contain two carbon atoms, such as acetic acid, ethanol and/or acetaldehyde. More particularly, this invention relates to the continuous conversion by the reaction of oxides of carbon, particularly CO, with hydrogen, to oxygenated carbon compounds containing two carbon atoms, in which control of the reaction avoids conditions which would cause the reaction to produce methane, $CO_2$ and/or carbon as the sole products.

It is known in the art to react CO and $H_2$ to produce a variety of products. In copending applications, Ser. Nos. 437,141, filed Jan. 28, 1974 now abandoned, and 541,661, filed Jan. 16, 1975 now abandoned, there are described processes for the manufacture of acetic acid, ethanol and/or acetaldehyde which involves reacting CO and $H_2$ in a rhodium metal catalyst bed. In U.S. Pat. No. 3,833,634, patented Sept. 3, 1974, ethylene glycol is the product of the reaction of CO and $H_2$ in the presence of a rhodium carbonyl complex. It is well known that many hydrocarbon products can be produced from the reaction of CO and $H_2$ over a methyl supported catalyst.

This invention is an improvement on the process described in Ser. No. 541,661, and is concerned with the continuous production of extremely valuable oxygenated carbon compounds containing two carbon atoms by the reaction of CO and $H_2$ in the presence of rhodium supported catalyst particles under conditions which provide high conversion of the reactants to such oxygenated carbon compounds and minimizes drastic fluctuations in temperature which could cause the reaction to shift solely to a methanation reaction or, in addition, form $CO_2$ and/or carbon. There is described herein the selection of conditions which optimize the control over the reaction of CO and $H_2$ to the oxygenated compounds whereby to minimize the formation of hydrocarbon products, $CO_2$ and carbon.

According to the disclosure of Ser. No. 541,661, synthesis gas containing carbon monoxide and hydrogen is contacted with a rhodium metal catalyst under reactive conditions of temperature, pressure, gas composition and space velocity correlated so as to favor the formation of a substantial proportion of acetic acid, ethanol, and/or acetaldehyde. The reaction efficiency, or selectivity, to these two-carbon atom compounds is invariably at least about 10%, and is usually upwards of about 25%; under the preferred conditions it exceeds 50% and, under optimum conditions, has reached 90% or more. Selectivity is defined herein as the percentage of carbon atoms converted from carbon monoxide to a specified compound or compounds other than $CO_2$.

The reaction is conducted at reactive conditions of temperature, pressure, gas composition and space velocity correlated so as to collectively produce acetic acid, ethanol, and/or acetaldehyde in an amount which is at least about 50 weight percent, preferably at least about 75 weight percent, of the two and more carbon atom compounds obtained by the reaction. Desirably, the reaction is conducted at these correlated conditions to achieve product efficiencies based on carbon consumption in excess of 10%, and frequently in excess of 50%. Ethyl esters and acetates formed are included as ethanol and acetic acid in determining productivities and selectivities. At optimum reaction conditions, and particularly at relatively low conversions, there is little conversion to three carbon atom and higher hydrocarbons and oxygenated hydrocarbons, and conversion to methane and methanol may readily be minimized. It is also possible, through variations in catalyst composition and reaction conditions, to direct the selectivity toward only one of the three products, e.g. acetic acid or ethanol.

Thus, the independent reaction variables are correlated, according to the invention of Ser. No. 541,661, so as to favor the formation of a substantial proportion of the desired two carbon atom oxygenated hydrocarbons (acetic acid, ethanol, and/or acetaldehyde). This proportion, expressed as carbon conversion efficiency, is usually upwards of 25% and frequently exceeds 50%.

This correlation is a combination of conditions which result in maintaining moderate reaction conditions to thereby limit the conversion of CO to not more than about one fourth, preferably not more than about one eighth. This may be achieved as indicated herein, in the optimum case, primarily by controlling a combination of high space velocity and temperature, but other factors (e.g. $H_2$/CO ratio, catalyst activity, pressure, bed geometry, etc.) also effect the conversion. At high conversions, it has been noted that higher carbon number hydrocarbons and oxygenated hydrocarbons are produced in excess, with a resulting loss in efficiency to two-carbon atom compounds.

The reaction is highly exothermic, with both the thermodynamic equilibrium and the kinetic reaction rates being governed by the reaction temperature. Average catalyst bed temperatures are usually within the range of about 150°–450° C., but for optimum conversions, bed temperatures are kept within the range of about 200°–400° C., typically about 250°–350° C.

As stated in Ser. No. 541,661, the reaction temperature is an important process variable, affecting not only total productivity but selectivity toward one or more of the desired carbon atom products. Over relatively narrow temperature ranges, as for example 10° or 20° C., an increase in temperature may somewhat increase total synthesis gas conversion, tending to increase the efficiency of ethanol production and decrease the efficiency of acetic acid and acetaldehyde production. At the same time, however, higher temperatures favor methane production, and apparently methane production increases much more rapidly at higher temperatures than do conversions to the more desirable two carbon atom products. Thus, for a given catalyst and with all other variables held constant, the optimum temperature will depend more on product and process economics than on thermodynamic or kinetic considerations, with higher temperatures tending to increase the production of oxygenated products by disproportionately increasing the co-production of methane.

In the discussions above, the indicated temperatures are expressed as average, or mean, reaction bed temperatures. Because of the highly exothermic nature of the reaction, it is desirable that the temperature be controlled so as not to produce a runaway methanation, in which methane formation is increased with higher temperature, and the resulting exotherm increases the temperature further.

The reaction zone pressure is desirably within the range of about 15 psig to about 10,000 psig, econimically within the range of about 300–5,000 psig. Higher reaction zone pressures increase the total weight of product obtained per unit time and likewise improve the selectivity toward two carbon atom compounds.

According to Ser. No. 541,661, the ratio of hydrogen to carbon monoxide in the synthesis gas may vary widely. Normally the mole ratio of hydrogen to carbon monoxide is within the range of 20:1 to 1:20, or preferably within the range of about 5:1 to about 1:5. In most of the experimental work reported the mole ratio of the hydrogen to carbon monoxide is somewhat less than 1:1. Increasing the ratio tends to increase the total rate of reaction, sometimes quite significantly, and has a small and favorable effect on production of two carbon atom products, but concurrently increases selectivity to methane. Increasing the hydrogen to carbon monoxide ratio also favors the formation of more highly reduced products, that is, ethanol, rather than acetaldehyde or acetic acid.

There are a number of problems that can arise in practicing the process of said copending applications. Because the reaction is exothermic and the catalyst is solid, the temperature of the reaction can rise rapidly unless care is taken to avoid this. When the reaction temperature becomes too high, the prime reaction products, as indicated above, are methane, carbon and/or carbon dioxide. However, if the mode selected for temperature control results in any increase in the temperature of the reaction without a compensating increase in the ability to remove the heat of reaction, the reaction will runaway with the aforementioned adverse effects.

There is described herein an improved process for making oxygenated carbon compounds containing two carbon atoms whereby the temperature control to avoid runaway reaction is achieved. There is also described a process for making such oxygenated carbon compounds wherein there is interrelated a variety of processing factors including a high conversion of the CO and $H_2$ gas mixture to said compounds and avoidance of catalyst poisoning with such compounds.

This invention involves a continuous process of making oxygenated carbon compounds containing two carbon atoms, such as acetic acid, ethanol and/or acetaldehyde. It is achieved by flowing, in a reaction zone, a gaseous mixture of CO and hydrogen about solid catalyst particles of rhodium combined with a particulate support. The essential features of the process include (a) controlling the temperature of the reaction zone by direct or indirect heat transfer cooling:

(b) using catalyst contaning particles which have a number average particle size of about 0.01 microns to about 1.27 centimeters (cm.);

(c) maintaining the temperature and pressure in the reaction zone from about 200° C. to about 450° C. and from about 100 pounds per square inch absolute (psia) to about 10,000 psia;

(d) defining the temperature difference between the catalyst and the heat transfer coolant by the equation $$\Delta T_{oa} = \Delta T_{cg}\left[1 + [M(1-e)\frac{d_t}{d_p}]\ [1 + \frac{h_{gw}\Theta}{k} + \frac{h_{gw}}{h_{wc}}]\right] \quad (1)$$

wherein $\Delta T_{oa}$ is the calculated overall temperature differential between the catalyst and the coolant; $\Delta T_{cg}$ is equal to $Q_r/h_{loc}a$ in which $Q_r$ is the total heat of reaction in calories/hour/cm$^3$ of catalyst bed, $h_{loc}$ is the heat transfer coefficient between the catalyst and the gas mixture measured in calories/hour/cm$^2$/° C.; $a$ is the square cm. of external particle surface of the catalyst per cu. cm. catalyst bed; M is 0 when the temperature is controlled by direct cooling and 1.5 when the temperature is controlled by indirect cooling; $d_t$ is the diameter in cm. of the cross-section of the reaction zone determined normal to the flow of said gas mixture; $d_p$ is the catalyst particle size in metric units; $e$ is the void fraction of the catalyst bed determined by the equation $1-(R_B/R_p)$ in which $R_B$ is weight of catalyst particles in reaction zone divided by its volume and $R_p$ is the weight of a single catalyst particle divided by its volume; $h_{gw}$ is equal to $h_{loc}$; $\theta$ is the thickness of the confinement about the reaction zone; $k$ is the thermal conductivity of said confinement determined in calories per hour-cm.-° C.; $h_{wc}$ is the heat transfer coefficient between the confinement and the coolant for indirect cooling; and (e) maintaining $\Delta T_{oa}$ at or less than T/[C(1-CONV)] wherein T is the temperature of the reaction zone in ° K., C is a number between about 7 to about 40 and CONV is the fractional conversion of the gas mixture to any other product.

Correlative with the above features of this inventive process is that at least about 3 mole percent of the gas mixture is converted to said oxygenated carbon compounds and the catalyst particles are maintained essentially free of liquid deposits of such compounds.

The process of this invention is concerned with the continuous manufacture of the oxygenated compounds containing two carbon atoms in a reactor in which heat is removed from the exothermic reaction by either direct or indirect heat transfer means. In the ideal case of direct heat transfer, a coolant medium, such as the reactant gas mixture, is provided to the reaction zone at a temperature low enough to withdraw exothermic heat of reaction and to maintain a stable temperature condition in the reaction zone. In the ideal case of indirect heat transfer, the coolant surrounds the confinement of the reaction zone, e.g., the reaction zone wall(s), the remove heat therefrom to maintain the same temperature condition.

It has been determined that when the overall temperature differential between the catalyst and such coolants (wherein said temperature differential is labeled "$\Delta T_{oa}$") is at or less than ($\leq$) the ratio T/[C(1-CONV)], wherein T is the temperature of the reaction zone in ° K., C is a number between about 7 to about 40, and "CONV" is the fractional conversion of the gas mixture to any other product (e.g., $CO_2$, $CH_4$, C, acetic acid, ethanol, acetaldehyde and methanol), the reaction is stable. However, when $\Delta T_{oa}$ is greater than T/[C(1-CONV)], the reaction will runaway, i.e., the temperature rise in the reaction will be so high that eventually the only products of the reaction will be $CO_2$, methane and/or carbon, and the desired oxygenated carbon compounds will not be formed.

Control of $\Delta T_{oa}$ to keep within above desired limits, i.e., at or less than T/[C(1-CONV)], can be achieved by a number of techniques.

For example, heat-removal from a fixed-bed reactor may be accomplished either directly by the injection of reactant gas at a lower temperature than the reaction temperature at the point of injection, or indirectly by contact of the hot gas with a cooler wall that is in turn cooled by contact with a heat-transfer medium such as Dowtherm ™. A third method is something of a hybrid between the direct and indirect modes of operation. In this method, the reactor consists of multiple beds of catalyst separated by heat-exchangers. All of the gas flows through each bed and absorbs heat as it passes through, the gas temperature rising as it does so. The gas is cooled by the heat-exchangers between the beds; these transfer the heat from the hot gas either to a heat-transfer medium like Dowtherm™ or to incoming reactant gas, which is preheated thereby.

This last hybrid case is a special case of the direct (gas-cooled) approach because the heat is not removed from the bed or by indirect transfer through a tube or vessel wall, as in the case of the indirect-cooled case.

The indirect-cooled reactor typically incorporates a number of tubes containing the catalyst, arranged in a compact parallel configuration, and separated and supported by suitable bulkheads through which the tube ends protrude for a fraction of a centimeter (cm.). This tube "bundle" is e.g., inserted in a cylindrical vessel of suitable length and diameter to completely surround the tube bundle. Dome-shaped end-bells may be fitted to the ends of the cylindrical vessel or "shell" and are in turn fitted with gas inlet and outlet pipes so that the gas enters the reactor in a direction parallel to the tubes.

The space between the tubes contains a liquid coolant such as water, kerosene, or proprietary heat-transfer fluids such as Dowtherm™. The coolant is pumped continuously on the outside of the tubes through the "shell-side" of the reactor from an entry pipe fitted to the cylindrical vessel side-wall near one end and leaves from a similar pipe fitted to the opposite end of the vessel at the side-wall. In particular designs, baffles may be fitted inside the reactor to direct the flow of the coolant. In this case, the catalyst tubes pierce and pass completely through all of the internal baffles.

Depending upon the application, the general direction of flow of the coolant may be in the same direction as that of the gas or in the opposite direction. It is desirable that the linear-velocity of the coolant be maintained as high as practicable to increase the efficiency of heat-transfer.

In operation, the reactant gases enter the reactor through the end-bell at the inlet end, divide and flow through the parallel catalyst tubes, wherein the reaction is conducted. The heat of reaction is transferred from the catalyst to the flowing gas, thence to the tube-wall, and through the tube wall into the coolant. The coolant flows through the reactor in the manner described above and leaves through the coolant exit pipe.

The direct cooled reactor relies upon the heat-capacitiy of the gas flowing through it to absorb and carry away the heat of reaction. The reactor will usually comprise a single large vessel which contains the catalyst and through which the gas flows.

The arrangement of necessary baffles and/or catalyst supports within the reactor depends upon its actual design and the mode of operation used to maintain the gas temperature within desired limits. There are several such arrangements that are typical.

In one such type of reactor, the catalyst is arranged within the reactor in several shallow beds, one on top of the other, with provision being made for additional cool gas to be injected between the beds, thereby cooling the main gas stream. The number of such beds depends upon the degree of temperature increase along the flow path of the gas that can be substained without adverse effect on product yields and selectivities. Thus, the temperature profile through the reactor in the direction of flow of the gas will assume a "saw-tooth" pattern as the gas is successively heated by the reaction and cooled by the injected cold gas.

In another configuration, several rows of gas sparger tubes are installed in a planar configuration normal to the longitudinal axis of the reactor, and the catalyst fills the remainder of the vessel without being physically separated into multiple shallow beds. The functional operation of the reactor is the same as in the preceding illustration.

In a third illustration, shallow catalyst beds within the reactor are separated by multi-tube heat-exchangers. The cool feed gas flows through the shell-side of the heat-exchangers, where it absorbs the heat of reaction from the gas that is leaving the catalyst beds that is flowing through the heat-exchanger tubes. This configuration suffers the disadvantage that a hot-spot in any one of the shallow catalyst beds will preheat the incoming gas to still higher temperatures, thus creating a situation in which this "thermal feed-back" can cause unstable operation and the possibility of runaway reaction.

Heat-transfer between the flowing gas and the catalyst particle compounds upon the following factors:

a. The temperature difference between the external surface of the catalyst particles and the gas, b. The external catalyst particle-surface to catalyst-bed volume ratio, c. The mass-velocity of the gas, expressed in terms of the mass of gas per unit catalyst bed cross-sectional area.

d. The physical properties of the gas, and e. The shape of the catalyst particles themselves.

The relationship between these factors has been studied by many researchers; and a useful summary reference is in *Mass Transport Phenomena*, by R. B. Bird, W. E. Stewart, and E. N. Lightfoot, John Wiley and Sons, Inc., New York, New York, 1960. The following development of the heat transfer coefficient is derived from this source.

The Reynolds number for a gas flowing in a fixed catalyst bed is given by $$Re = G/au\phi \tag{2}$$

where

G is the mass-velocity of the gas, grams gas/hr./cm² of catalyst bed cross-section, $a$ is the solid particle surface area per unit of bed volume in reciprocal cm, $u$ is the viscosity of the gas in consistent units, and $\phi$ is a geometric shape factor, which is defined as 1.0 for spheres, 0.91 for cylinders, and other values for other shapes.

The Reynolds number is used to define a "$j_H$" factor which is subsequently used in the calculation of the local (i.e., catalyst-to-gas) heat-transfer coefficient, $h_{loc}$:

$$j_H = 0.91 \text{ Re}^{-.51}\phi \text{ for Re less than 50}$$

$$j_H = 0.61 \text{ Re}^{-0.41}\phi \text{ for Re equal or greater than 50} \tag{3}$$

$$h_{loc} = j_H C_P (\text{Pr})^{-0.67} G \tag{4}$$

where $h_{loc}$ has units of cal/hr/cm²/° C.

$C_P$ is bulk gas heat capacity, cal/gram/° C. and

Pr is the Prandtl number for the gas.

The Prandtl number for most gases lies between about 0.6 and 0.9 and changes very little with temperature or pressure. An average value of 0.8 may be used with little error in all normal cases.

The heat-transfer coefficient thus calculated portrays the resistance to heat-transfer between the flowing gas and the outer surfaces of the catalyst. It is related to the temperature difference by the ratio $$Q_r/h_{loc}a, \text{ defined above.} \quad (5)$$

The size of the catalyst particle has, of course, a direct bearing upon the catalyst-bed surface-to-volume ratio (the "$a$" term in the above analysis). In general, smaller catalyst particles give rise to higher heat-transfer coefficients and lower $\Delta T$'s. Increasing the mass-velocity has the same effect.

At this point, it is desirable to consider the impact of this temperature difference upon the thermal stability of the reactor in order to assess its importance. As stated herein, there is a maximum allowable overall $\Delta T$ between the catalyst particle surface and the heat-sink, which will be the gas itself for a direct-cooled reactor and the Dowtherm or other coolant for the indirect case.

The most important single criterion for stable operation of a catalytic reactor can be stated in this way for exothermic reactions:

The slope of the heat-generation vs. reaction temperature line must be less than that of the heat-removal vs. reaction temperature line.

Stated differently, an increase in the $\Delta T$ between the heat-source (the reaction) and the heat-sink (the gas or coolant) must increase the heat-removal capabilities of the system to a greater degree than it increases the heatgeneration capabilities.

For a single first-order reaction it can be shown that there is a maximum allowable $\Delta T$ for stable operation that is defined by $$\Delta T_{max} = \frac{RT^2}{E_a} \frac{1}{1 - CONV} \quad (6)$$

where $T$ is a reaction temperature, R is the gas constant (1.987 cal/gmol/° C.) $E_a$ is the apparent activation energy for the reaction in cal/gmol, and CONV is the fractional conversion of the gas. In this equation (6), $RT^2/E_a$ is equal to C referred to above. The impact of the conversion term is apparent if one recognizes that at complete conversion the allowable temperature differential is infinite because there is no potential for the reaction to runaway.

While the above criterion is not exact for reactions other than first order, it is sufficiently close to the correct value for other types of that it can be used effectively.

While the activation energies for the reactions under consideration are not known and will change in any event from one catalyst to another, it is generally true that for many reactions of industrial interest the following approximate relationship holds:

$$E_a/RT \approx 20 \quad (7)$$

whence the stability criterion reduces to (at low conversion)

$$\Delta T_{max} = T/20.$$

At an average temperature of 350° C. (623° K.), the maximum allowable temperature difference between the catalyst surface and the heat-sink is thus seen to be of the order of 30° C. Normally a safety factor is applied to this number to account for reaction rate differences in different parts of the catalyst bed, and a desirable limit is of the order of 20° C. Obviously, actual design calculations should consider the actual activation energy if at all possible, but even at the lower temperatures anticipated for this process — of the order of 200° C. — the approximate criterion leaves room for safety if 20° C. is used as the maximum temperature difference. In the following 20° C. will be used.

As the prototype reactor for the purposes of this analysis, the conventional shell-and-tube reactor is used and the relationship between the catalyst particle diameter, the tube diameter, the tube length, the space velocity, and the mass velocity is developed. In this context, one needs to define the relationship between mass-velocity and space-velocity. The former determines the heat-transfer characteristics of the system, and the latter the degree of conversion at a given productivity. Mass-velocity is defined as $$G = W/A \text{ gms/hr/cm}^2 \text{ of bed cross-section.} \quad (9)$$

In the above, $W$ is weight of gas flowing in grams/hour, and $A$ is cross-sectional area of bed measured normal to gas flow. Space velocity is defined as $$SV = \frac{22,400W}{(MW)(L)(A)} \quad \begin{array}{l}\text{standard cm}^3/\text{cm}^3 \text{ of catalyst bed} \\ \text{where } MW \text{ is the molecular weight} \\ \text{of the gas, and } L \text{ is bed length}\end{array} \quad (10)$$

Therefore $$SV = \frac{22,400G}{(MW)(L)} \quad (11)$$

Thus one may specify any two of the three following quantities: space velocity, mass velocity or bed length, but not all three.

For the indirect-cooled converter, the overall temperature differential for purposes of both heat-transfer and thermal stability is the sum of several individual differences: $\Delta T_{oa} = \Delta T_{cg} + \Delta T_{gw} + \Delta T_w = \Delta T_{wc}$ (12)

where $\Delta T_{oa}$ is the overall temperature differential $\Delta T_{cg}$ is the temperature difference between catalyst and gas $\Delta T_{gw}$ is the temperature difference between gas and wall $\Delta T_w$ is the temperature difference between the inner and wall of the reactor (through the metal)

$\Delta T_{wc}$ is the temperature difference between the reactor wall and the Dowtherm ™ or other coolant.

The individual temperature differences listed above are all desirable in terms of the $\Delta T_{cg}$, the ratio of reactor diameter to catalyst particle diameter $d_t/d_p$, the heat-transfer coefficients at the reactor wall, the thermal conductivity of the wall metal, and its thickness.

Assume that the inside heat-transfer coefficient at the reactor wall is the same as that between the gas and the catalyst particle, experience has shown this to be a valid assumption, and assume that the turbulence level at the wall is much the same as that adjacent to the catalyst, it then can be shown that $$\Delta T_{gw} = 1.5(1-e) \cdot \frac{d_t}{d_p} \cdot \Delta T_{cg} \quad (13)$$

where $d_t$, $d_p$, and $e$ are defined above.

$$\Delta T_w = \frac{h_{gw}}{k/\theta} \cdot \Delta T_{gm} \quad (14)$$

$$\Delta T_{wc} = \frac{h_{gw}}{h_{wc}} \cdot \Delta T_{gw} \quad (15)$$

where k is thermal conductivity and T is wall thickness

Hence, collecting and combining terms, the overall temperature difference is given by:

$$\Delta T_{oa} = \Delta T_{cg}\left[1 + [1.5(1-e)\frac{d_t}{d_p}][1 + \frac{h_{gw}\theta}{k} + \frac{h_{gw}}{h_{wc}}]\right] \quad (16)$$

In a typical example, $d_t/d_p$ might be 5, $e = 0.5$, $h_{gw}\theta/k$ of the order of 0.25, and $h_{gw}/h_{wc}$ of the order of 0.5. The overall temperature difference in this case would be $$\Delta T_{oa} = \Delta T_{cg}[1 + [1.5(0.5)(5)][1 + 0.25 + 0.5]] = 7.56 \cdot \Delta T_{cg}$$

If the 20° C. maximum temperature difference for stable operation were applicable, the allowable difference between catalyst and gas would thus be 20/7.56, or 2.65° C. It is apparent that the controlling factors in this calculation are the ratio of the reactor diameter to the particle diameter ratio and the $\Delta T_{cg}$, discussed above.

If very small catalyst particles are necessary for reasons of heat removal from the catalyst or to minimize the importance of internal pore diffusion, one obviously has the choice of utilizing small diameter reactors or high mass velocities to maintain the overall temperature differential within bounds.

An example at this point will clarify these relationships. Consider the following process conditions:

| Assumptions | |
|---|---|
| Productivity: | 0.48 gms/cm³/hr Ethanol at 80% efficiency (remainder methane) |
| Heat-load: | 890 cal. / cm³-hr |
| Mass Velocity: | 3906 gms / hr-cm² |
| Catalyst: | .4763 cm spheres |
| Tubular reactor: | 762 cm length × 2.54 cm inside diameter (ID) × 3.81 cm. outside diameter (OD) |
| Thermal Conductivity: | 140.59 cal/cm²/hr/(° C/cm) |
| Shell-side Heat-Transfer Coefficient: | 108.5 cal./hr/° C/cm² |

From the relationship developed above, the gas-side heat-transfer coefficient is about 81.39 cal./hr/° C./cm² and the catalyst-to-gas temperature difference is predicted to be 1.8° C. Further assuming that the void fraction is 0.5, the ratio of tube-to-catalyst diameter is 5.33, the tube-wall thickness term is 0.367, and the ratio of gas-side to coolant-side heat transfer coefficient is 0.75, then the overall temperature difference is $$T_{oa} = 1.8 (1 + [1.5(0.5)(16/3)][1 + 0.367 + 0.75])$$
$$= 18.0° C.$$

Thus the conclusion would be that such a reactor would be thermally stably and feasible; although it might not be the economic optimum.

If, instead of a 0.4763 cm. catalyst particle, there is chosen a 0.1588 cm particle, the gas-side heat-transfer coefficient would have increased to 130.22 and the temperature difference between catalyst and gas would be only about 0.5° C., but the diameter ratio would have increased to 16. In this case, the overall temperature difference would be $$\Delta T_{oa} = 0.4 [1 + (12) (1 + 0.59 + 1.2)] = 13.8° C.$$

Improvement is seen as a result of the change and the reactor would still be a feasible one. However, the pressure drop through the reactor is roughly proportional inversely to the particle size, and would thus be nearly three times as great.

To circumvent the pressure drop problem, one might reduce the mass-velocity (pressure-drop is proportional to the cube of mass-velocity if space velocity is held constant). Thus, in order to achieve the same pressure drop, the mass-velocity would be reduced from 3906 to 2709. The gas-side heat-transfer coefficient is about 103.1 cal/hr/cm²/° C., and the catalyst-to-gas temperature difference is now about 0.5° C. The overall temperature difference is now:

$$\Delta T_{oa} = 0.50 [1 + (12) (1 + 0.465 + 0.95)] = 15.0° C.$$

Thus, some improvement in overall temperature differential of 18° C. has been obtained by decreasing catalyst particle size at no expense in pressure-drop. The improvement overall is not as great as that between catalyst and gas because of the adverse offsetting effect of the tube diameter-to-particle diameter ratio. Nevertheless, the improvement is characteristic of the simultaneous change of particle size and mass-velocity.

Again using equation (16), one can easily determine the effect of tube diameter upon the overall temperature differential. Returning to the basic case involving a mass-velocity of 3906 and the 0.4763 cm catalyst particle, but using a tube diameter of 3.81 cm instead of the 2.54 cm. tube assumed above, the following results:

$$\Delta T_{oa} = 1.8 (1 + [1.5(0.5) (1.5) (5.33)][1 + 0.367 + 0.75]) = 24.7° C.$$

The change from a 2.54 cm tube to a 3.81-cm tube diameter increased the overall temperature differential from 18° C. to nearly 25° C. In addition, the ratio $d_t/d_p$ has been increased from 5.33 to 8.0.

Next, in considering the effect of these analyses upon the tube length required to obtain a stipulated space-velocity, which in turn controls the conversion level in the reactor, assume that the catalyst produces ethanol at a productivity of 0.48 gm/hr/cm³ at an overall efficiency of 80%. In that case, 7.5 moles of synthesis gas will be required for each mole of ethanol produced. If the required conversion is, say, 12 percent, the total moles of synthesis gas required will be $$\text{Moles of synthesis gas} = \frac{30}{46} \times \frac{7.5}{.12} = 40.76$$

and the required space-velocity (SV) will be 22400 (40.76), i.e., 14633 standard cm$^3$/hr/cm$^3$.

The required catalyst-bed depth for each of the cases above can be calculated easily from equation (11), using a molecular weight of the gas of 10.7; this latter number is the mean molecular weight of a mixture consisting of 2 mols of CO and 4 mols of hydrogen. Thus, for the base case cited first in the example $$SV = \frac{22400G}{(MW)(L)}, \quad (17)$$

$$L_{req} = \frac{22400G}{(MW)(SV)} = \frac{(22400)(3906)}{(10.7)(14633)} \text{ and } L_{req} = 559 \text{ cm}$$

To calculate the pressure drop associated with each of these cases, a very useful approximate relationship is $$\Delta P = \frac{1.97(1^{-9})G^2L}{\rho_g d_p} \quad (18)$$

Where
$\rho_g$ is gas density, gm/cm$^3$, and
$d_p$ is particle diameter, cm.

The limiting worst case will be for relatively low pressures, such as 500 psi. At, for example, 325° C., and at a molecular weight of 10.7, the gas density will be 0.0077 gms/cm$^3$, and the pressure drops for the cases cited above may be calculated. After performing similar calculations for each of the example cases, we may finally summarize the results for each, at SV = 14633:

Table I

| Catalyst Size, cm. | Mass Velocity, gms/cm$^2$/hr | Tube Diameter, cm. | $\Delta P$, gm/cm$^2$ | Tube Length, cm. | $\Delta T_{cg}$, (° C) |
|---|---|---|---|---|---|
| .48 | 3906 | 2.54 | 4581 | 559 | 18.0 |
| .16 | 3906 | 2.54 | 13752 | 18.34 | 13.8 |
| .16 | 2709 | 2.54 | 4581 | 12.72 | 15.0 |
| .48 | 3906 | 3.81 | 4581 | 18.34 | 24.7 |

Although these pressure-drops are rather high in comparison to normal plant practice, design calculations using actual activation energies should optimize the reactor design to reduce these pressure drops. Operations at higher pressures would, of course, reduce pressure drops by increasing gas density.

Finally, it is apparent from the summary of the illustrations given in Table I that there can, in principle, be a reduction in both the overall temperature differential and the pressure drop by simultaneously reducing catalyst particle size, tube diameter, and tube length. It is also apparent that one cannot ignore practical matters in this respect: a reactor designed to accommodate 0.0625 cm catalyst pellets in 0.6350-inch diameter tubes at a mass-velocity of 488 gm/cm-hr would exhibit an overall $\Delta T$ (on the same basis as before) of only about 8° C., a bed-depth of 70 cm, and a pressuredrop of less than 70 gms/cm$^2$, but except as a single-tube laboratory reactor it would not be considered an ideal design since such a 3-foot high reactor covering perhaps an acre of ground would not be considered optimum, even if its characteristics are admirable.

The direct-cooled converter makes practicable the use of small catalyst particles and low mass velocities without the necessity of using small tubes to achieve adequate heat transfer.

Functionally, the direct-cooled reactor, as mentioned above, is a series of adiabatic beds, between which the temperature is lowered either by injection of cooler gas or by indirect heat-exchange. Whether the beds are phycially separate or not is immaterial to the concept. It is significant to this invention that the heat-sink — in this case the bulk gas, there being no coolant involved — not be at a temperature at which the critical differential temperature for thermal stability is exceeded.

The following is used as a criterion for stability in the direct-cooled reactor $$\Delta T_{cg} \leq \frac{RT^2}{E} \cdot \frac{1}{1 - \text{CONV}} \quad (19)$$

From the heat-transfer studies, it is evident that one may operate a direct-cooled reactor at a very much lower mass-velocity without exceeding the stability criterion than is possible with the indirectly-cooled case. In fact, it is only with catalyst particle sizes of the order of 0.9525 cm diameter at mass-velocities as low as 488 gms/cm$^2$/hr that the temperature difference finally becomes significant in comparison to the stability criterion. Using catalyst particles smaller than 0.96 cm., then G = 488 may be effectively used as a design criterion. Mass-velocities lower than this may introduce problems in other areas (like non-ideal flow-patterns because of low-pressure drop through the bed, difficulty in properly mixing the injected cool gas, and the like).

The minimum total length (L) of the catalyst-bed is calculated from equation (17) as follows:

$$L = \frac{22400(488)}{(10.7)(14633)} = 69.815 \text{ cm}$$

Provided that the heat of reaction could be effectively removed from a bed of this shallow depth, such a bed is technically feasible. However, it almost certainly would not be economical because the bed diameter would be enormous. Nonetheless, the 488-value for mass-velocity is an effective minimum within the concept of this process for the synthesis gas reaction to produce ethanol, acetic acid, and acetaldehyde. It additionally serves to illustrate the advantage from a stability standpoint of the direct-cooled converter over the indirect-cooled case.

In the practice of this process, the rhodium catalyst is rhodium metal provided in the reaction zone as particles, such as placing particles of rhodium in the reaction zone, generally supported by an inert porous particulate packing material, or depositing rhodium onto a particulate support material and place the supported rhodium into the reaction zone or a combination of these techniques.

However, the invention is most favorably practiced when the rhodium metal catalyst is in a highly dispersed form on a particulate support. On the basis of experience to date the amount of catalyst on the support should range from about 0.01 weight percent to about 25 weight percent, based on the combined weight of the metal catalyst and the support material. Preferably, the amount of catalyst is within the range of about 0.1 to about 10 weight percent.

A wide variety of support materials has been tested. A relatively high surface area particulate support, e.g., one having a surface area upwards of about 1.0 square meters per gram (BET low temperature nitrogen adsorption isotherm method), is preferred, desirably upwards of about 10 square meters per gram, although surface area alone is not the sole determinative variable. Based on research to date, silica gel is preferred as the catalyst base or support, with graphite, graphitized carbon, alpha-alumina, manganese oxides, magnesia, eta-alumina, gamma-alumina, and active carbon being progressively less desirable. Zeolitic molecular sieves, primarily the higher silica-to-alumina crystalline zeolites, also have promise.

The rhodium metal may be deposited onto the base or support by any of the techniques commonly used for catalyst preparation, as for example impregnation from an organic or inorganic solution, precipitation, coprecipitation, or cation exchange (on a zeolite). Numerous specific embodiments of catalysts preparatory techniques are described in the Examples below; it suffices for the present to say that an inorganic or organic rhodium compound is appropriately contacted with the support material, and the support then dried and heated, the latter advantageously under reducing conditions, to form the finely dispersed rhodium metal.

The following illustrates the preparation of supported rhodium metal catalysts on a variety of high surface area supports.

The catalysts tested are all prepared by essentially the same sequence of steps: An aqueous solution of the desired component is impregnated on the support; the impregnated support is carefully dried; the metal salt is reduced slowly in a flowing hydrogen atmosphere. When metal components are impregnated as nitrate salts, a pyrolysis step preceeds the hydrogen reduction step. In most cases, rhodium is impregnated as a $RhCl_3$ solution. This is illustrated by the following.

Rhodium trichloride (22.58 gm, 41.93% Rh) is dissolved in 240 ml of distilled water at ambient temperature. Davison TM Grade 59 silica gel (200.0 gm, 3-6 mesh) is placed in a vacuum flask. The top of the flask is sealed with a rubber septum, and the flask is evacuated through the side arm. A syringe needle is then used to inject the rhodium solution onto the evacuated support. When addition is complete, the impregnated support is allowed to stand at one atmosphere for ca. 30 minutes. It is then carefully dried in a nitrogen atmosphere: 80° C. (1 hr); 110° C. (2 hrs); 150° C. (2 hrs). The dried, impregnated support is placed in a quartz tube through which hydrogen is continuously passed. The temperature is raised to 450° C. and held at that value for 2 hours. The reduced catalyst is cooled to ambient temperature in an atmosphere of flowing nitrogen. The following Table II illustrates a variety of rhodium supported catalysts as taken from Ser. No. 541,661:

TABLE II

DESCRIPTION OF CATALYSTS

| Metal, %'s | Support | Dispersion, % | Metal Origin(s) |
| --- | --- | --- | --- |
| Rh (5%) | Davison$^{TM}$ 59 Silica Gel | 22 | $RhCl_3$ |
| Rh (2.5%) | Norton $^{TM}$ LA 6173 | 58 | $RhCl_3$ |
| Rh (5%) | Pittsburgh $^{TM}$ Carbon | 77 | Matthey-Bishop Catalyst |
| Rh (2.5%) | Norton $^{TM}$ LA 6173 | 86 | $RhCl_3$ |
| Rh (2.5%) | Davison $^{TM}$ 59 Silica Gel | 21 | $Rh(NO_3)_3$ |

The reactor used in Example 3 below is a bottom-agitated "Magnedrive" autoclave of the J. M. Berty design with a centrally positioned catalyst basket and a side product effluent line. It is of the type depicted in FIG. 1 of the paper by Berty, Hambrick, Malone and Ullock, entitled "Reactor for Vapor-Phase Catalytic Studies", presented as Preprint 42E at the Symposium on Advances in High-Pressure Technology — Part II, Sixty Fourth National Meeting of the American Institute of Chemical Engineers (AIChE), at New Orleans, Louisiana, on March 16-20, 1969 and obtainable from AIChE at 345 East 47 Street, New York, N.Y. 10017. A variable speed, magnetically driven fan continuously recirculates the reaction mixture over the catalyst bed.

The following examples serve to provide specific illustrates of this invention.

EXAMPLE 1 — The Indirect-cooled Converter

The reactor of this example is a stainless steel tube of 2.54 cm. internal diameter, with a wall thickness of 0.635 cm. The length is 762 cm. The tube is packed with catalyst prepared as described above, using 0.476 cm. diameter silica gel pellets as support.

The reactor is fitted with a boiling Dowtherm$^{TM}$ jacket and suitable flow, temperature, and pressure controls. The shell-side heat-transfer coefficient in this reactor is 108 cal/cm$^2$/hr/° C. The temperature profile in the tube is nearly isothermal, with the gas entering at 315° C. and reaching a peak temperature of 323° C. at a distance 137 cm. from the inlet. The mean productivity of $C_2$ chemical is 0.48 gms/hr-cm$^3$ of reactor volume (expressed as ethanol or ethanol equivalents), and the heat load in the tube is therefore 922 cal/cm$^3$/hr.

The gas feed rate is 7631 gms of synthesis gas, comprising a CO:$H_2$ ratio of 3:1. The mass velocity is thus 1506 gms/cm$^2$/hr.

The Prandtl number of the gas is 0.8, the heat capacity is 0.7 cal/gm/° C., the viscosity is 2.16 grams/hr/cm. The Reynolds Number of the gas flowing through the bed is 110.67.

The stability criterion for the catalyst had as previously determined, is T° K/28, in accordance with equation (6) above. At the peak temperature of 323° C., the maximum temperature difference for stable operation is thus 596/28, or 21.3° C.

At the peak temperature in the tube (323° C.), the adjacent jacket Dowtherm$^{TM}$ temperature is 308° C., and the overall temperature difference is thus 15° C.

It is seen that the observed temperature difference is less than the calculated maximum value of 21.3° C., and the reactor performs smoothly and under control.

EXAMPLE 2

The system of Example 1 is operated with a slowly circulating counter-current coolant system in which the shell-side heat-transfer coefficient is not 108 cal/cm$^2$/hr/° C., as before, but 52. Heat transfer is thus severly impeded.

If stable operation could be sustained, one may calculate using the method described earlier that the observed temperature difference would be 24° C., in excess of the maximum permissible value of 21.3° C. One predicts that the system cannot be stable under these circumstances.

In the experiment, coolant temperature is slowly raised from a starting value of about 250° C. until a temperature in the coolant of about 300° C. is reached adjacent to the gas peak temperature of about 323° C. At this point, temperature control is lost, the gas temperature rises abruptly to over 600° C. (the limit of the temperature recorder), and the major reaction product is observed to be methane.

EXAMPLE 3: The Direct-Cooled Reactor

For this example, a catalytic gas autoclave of the J. M. Berty design is utilized and is charged with 200 grams of the catalyst of Example 1.

The feed gas (3:1 CO/H$_2$) is fed to the catalyst at a rate of 600 standard liter per hour, which is equivalent to a space velocity of 3000 hr$^{-1}$. The impeller of the autoclave is run at 1500 RPM, which results in a mass velocity in excess of 4000 gms/cm$^2$/hr. The gas temperature leaving the autoclave is 275° C., and approximately 10 gms/hour of C$_2$ products are produced. The conversion of the feed gas is about 1.7 mole percent. The total heat of reaction is about 184 kcal./hr.

If the reactor were to be operated truly adiabatically by means of heating mantle that would compensate for heat losses to the atmosphere, the adiabatic temperature rise would be nearly 34° C., in excess of maximum for stable operation. However, some of the heat of reaction is allowed to escape from the autoclave to the atmosphere, the inlet gas temperature is raised to 260° C., and the overall temperature difference is now the 15° between the gas leaving and entering plus the approximately 3° calculated to exist between the catalyst surface and the gas, or 18° C. total. The maximum allowable is T° K./28, or 19.6° C. It is seen that the operation is now stable, but just barely so.

Still more heat is allowed to escape from the reactor, and the inlet temperature is rasied again to compensate. The inlet temperature is now observed at 265° C., and the operation is quite stable in all respects.

What is claimed is:

1. The continuous process of making oxygenated carbon compounds containing two carbon atoms such as acetic acid, ethanol and acetaldehyde, by the exothermic reaction under controlled temperature conditions in a confined reaction zone, of a carbon monoxide and hydrogen gas mixture flowing about a fixed bed of solid catalyst particles of rhodium combined with a particulate substrate; controlling the temperature in the reaction zone by either direct or indirect heat transfer cooling; said particles of the bed have a number average particle size of about 0.01 microns to about 1.27 cm.; maintaining the temperature in the reaction zone from about 200° C. to about 450° C. and the pressure in the reaction zone from about 100 psia to about 10,000 psia wherein the selectivity to two carbon atom compounds exceeds 50 percent, and at least 50 weight percent of the two carbon atom compounds produced are acetic acid, ethanol and/or acetaldehyde; the temperature difference between the catalyst and the heat transfer coolant is defined by the equation:

$$\Delta T_{oa} = \Delta T_{cg}\left[ 1 + [M(1-e)\frac{d_t}{d_p}][1 + \frac{h_{gw}\theta}{k} + \frac{h_{gw}}{h_{wc}}] \right]$$

wherein $\Delta T_{oa}$ is the calculated overall temperature differential between the catalyst and the coolant; $\Delta T_{cg}$ is equal to $Q_r/h_{loc}a$ in which $Q_r$ is the total heat of reaction in calories/hour/cm.$^3$ of catalyst bed, $h_{loc}$ is the heat transfer coefficient between the catalyst and the gas mixture measured in calories/hour/cm.$^2$/° C.; $a$ is the square cm. of external surface of the catalyst per cu. cm. catalyst bed; M is 0 when the temperature is controlled by direct cooling and 1.5 when the temperature is controlled by indirect cooling; $d_t$ is the diameter in cm. of the cross section of the reaction zone determined normal to the flow of said gas mixture; $d_p$ is the catalyst particle size in metric units; $e$ is the void fraction of the catalyst bed determined by the equation $1-(R_B/R_p)$ in which $R_B$ is weight of catalyst particles in reaction zone divided by its volume and $R_p$ is the weight of a single catalyst particle divided by its volume; $h_{gw}$ is equal to $h_{loc}$; $\theta$ is the thickness of the confinement about the reaction zone, $k$ is the thermal conductivity of said confinement determined in calories per hour-cm.-° C.; $h_{wc}$ is heat transfer coefficient between the confinement and the coolant for direct cooling; and maintaining $\Delta T_{oa}$ at or less than $T/[C(1-CONV)]$ wherein T is the temperature of the reaction zone in ° K., C is a number between about 7 to about 40 and CONV is the fractional conversion of the gas mixture to any other product providing for a percent mole conversion of the gas mixture to such oxygenated carbon compounds of at least 3, and maintaining said catalyst particles essentially free of deposits of such compounds in liquid form.

* * * * *